United States Patent [19]

Osawa

[11] Patent Number: 5,476,795
[45] Date of Patent: Dec. 19, 1995

[54] METHOD FOR EVALUATING DEGREE OF DISPERSION OF INORGANIC MATERIAL IN COMPOSITE MATERIAL

[75] Inventor: Takashi Osawa, Shiga, Japan

[73] Assignee: Murata Manufacturing Co., Ltd., Japan

[21] Appl. No.: 360,175

[22] Filed: Dec. 20, 1994

Related U.S. Application Data

[63] Continuation of Ser. No. 37,223, Mar. 26, 1993, abandoned.

[30] Foreign Application Priority Data

Mar. 27, 1992 [JP] Japan .................................. 4-070949

[51] Int. Cl.$^6$ .................................................. G01N 33/00
[52] U.S. Cl. ......................... 436/155; 436/158; 436/160; 436/182; 73/149; 73/866
[58] Field of Search ................................. 436/155, 158, 436/160, 182; 73/149, 866

[56] References Cited

U.S. PATENT DOCUMENTS

| | | | |
|---|---|---|---|
| 4,185,001 | 1/1980 | Machurat et al. | 260/42.37 |
| 4,187,210 | 2/1980 | Howard, Jr. | 260/42.14 |
| 4,565,669 | 1/1986 | Collins et al. | 436/155 |

*Primary Examiner*—James C. Housel
*Assistant Examiner*—Rachel Heather Freed
*Attorney, Agent, or Firm*—Ostrolenk, Faber, Gerb & Soffen

[57] ABSTRACT

A method for evaluating a degree of dispersion of an inorganic material in a composite material comprising an organic material having dispersed therein the inorganic material, the method comprising the steps of: forming a block sample of the composite material; dividing the block sample into a plurality of unit volume pieces; incinerating each of the unit volume pieces under an oxidative atmosphere; quantitatively determining the ash content of each of the unit volume pieces; and calculating the scatter of the inorganic material content within the plurality of unit volume pieces.

8 Claims, No Drawings

METHOD FOR EVALUATING DEGREE OF DISPERSION OF INORGANIC MATERIAL IN COMPOSITE MATERIAL

This is a continuation of application Ser. No. 08/037,223 filed on Mar. 26, 1993, now abandoned.

FIELD OF THE INVENTION

The present invention relates to a method for evaluating a degree of dispersion of an inorganic material in a composite material comprising an organic material having dispersed therein the inorganic material, for example, resin materials used as exterior covering materials for electronic parts.

BACKGROUND OF THE INVENTION

Examples of composite materials for covering electronic parts include epoxy resin matrices mixed with silica (silicon dioxide). Silica is incorporated because the use of an epoxy resin alone as an exterior covering material results in an increased cost of the electronic components and an exterior covering of insufficient mechanical strength, since epoxy resins are brittle if used alone.

From the standpoint of obtaining enhanced mechanical strength, silica must be uniformly dispersed in the resin matrix. This kind of composite materials for use as an exterior covering of electronic components are therefore prepared by, for example, stirring silica and the resin by means of an appropriate stirring machine, so as to attain uniform dispersion of silica in the resin matrix. Further, it is necessary to evaluate the degree of dispersion of silica in the composite material as a final product.

Representative examples of the methods now available for evaluating the degree of dispersion include:

(1) A liquid composite material is poured into a container having a small-diameter nozzle at the bottom. The composite material drips from the nozzle and forms a thread due to its viscosity. The higher the degree of the silica, the longer the thread. The degree of dispersion can thus be evaluated by visual estimation of the length of the thread; and (2) A composite material is solidified once, and a solid sample is cut. The cut area is visually observed under a microscope, etc. to obtain a value of the dispersed particles per unit area or the number of the dispersed particles per unit area. The results are used to create histogram, and the degree of dispersion is evaluated from the shape of the histogram.

Method (1) has a problem in that quantitative determination is impossible. The evaluation according to either method is not absolute but relative. The evaluation methods (1) and (2) assume subjectiveness. In particular, method (2) fails to make an evaluation throughout the whole material.

SUMMARY OF THE INVENTION

An object of the present invention is to provide the method for evaluating a degree of dispersion of an inorganic material in an organic composite material quantitatively and absolutely.

Other objects and effects of the present invention will be apparent from the following description.

The present invention relates to a method for evaluating a degree of dispersion of an inorganic material in the composite material comprising an organic material having dispersed therein the inorganic material, the method comprising the steps of:

forming a block sample of the composite material;

dividing the block sample into a plurality of unit volume pieces;

incinerating each of the unit volume pieces in an oxidative atmosphere;

quantitatively determining the ash content of each of the unit volume pieces; and calculating the scatter of the inorganic material content within the plurality of unit volume pieces.

DESCRIPTION OF THE PREFERRED EMBODIMENTS

Each unit volume piece leaves only the ash on incineration. The degree of scatter of the inorganic material in the block sample can be calculated from the ash content of each unit volume piece, from which the degree of dispersion of the inorganic material in the composite material can then be evaluated quantitatively.

The organic materials and the inorganic materials constituting the composite materials to be subjected to the method of the present invention are not particularly limited.

The block sample is divided into a plurality of unit volume pieces, and preferably the whole of the sample is divided and subjected to the subsequent incineration and quantitative determination.

The number and shape of the unit volume pieces are not particularly limited as long as they have the same volume as each other. By increasing the number of the unit volume pieces, the sensitivity of the evaluation can be higher.

The conditions for the incineration is not particularly limited as long as all the organic materials contained in the composite material are burnt out. The incineration conditions can be selected from the range of 400° C. for 1 hour to 600° C. for 20 hours. The oxidative atmosphere is not particularly limited, as long as the incineration is completed, and include, for example, air and oxygen.

The quantitative determination of the ash content can be conducted by any conventional manner such as an electronic balance, fluorescent X-ray analysis, infrared spectroscopic analysis, e.g., FT-IR (Fourier transform infrared spectroscopy), etc.

The calculation of the scatter of the inorganic material content can be made by any method such as a coefficient of variation and an entropy of partition, and the method of calculation of the scatter is not particularly limited.

The method according to the present invention will now be illustrated in greater detail with reference to Examples, but it should be understood that the present invention is not construed as being limited thereto. All the parts are by weight unless otherwise specified.

EXAMPLE 1

| Organic Material: | |
| --- | --- |
| Bisphenol A type epoxy resin | 100 parts |
| Methylene terephthalate (curing | 86 parts |

-continued

| | |
|---|---|
| agent) | |
| Defoaming agent | 2 parts |
| Inorganic Material: | |
| Spherical silica (average particle size: 5 μm) | 100 parts |

The above components were stirred in a vacuum mixer for either 5 minutes or 100 minutes to prepare thermosetting composition Samples A and B, respectively. Each sample was poured into a mold (10×10×5 mm) and cured by heating at 100° C. for 24 hours to prepare Blocks 1 or 2, respectively.

The whole of each block was diced to a size of 1×1×1 mm by means of a dicer to obtain unit volume pieces 1a, 1b, . . . or 2a, 2b, . . . , respectively.

The pieces were individually incinerated under conditions selected from the range of 400° C. for 1 hour to 600° C. for 20 hours. By the incineration, all the organic materials were burnt out, leaving only the silica as an ash. The ash was determined for each piece, preferably to a precision of 0.1 μg with an electron balance.

The degree of scatter of the ash content among pieces 1a, 1b, . . . of block 1 and that among pieces 2a, 2b, . . . of block 2 were obtained as a coefficient of variation (i.e., standard deviation/mean value, hereinafter abbreviated as CV value). The results obtained are shown in Table 1 below.

TABLE 1

| Sample | Stirring Time (min) | CV Value in Silica Content among Unit Volume Pieces (%) |
|---|---|---|
| A | 5 | 42.1 |
| B | 100 | 3.4 |

As is apparent from the results in Table 1, Sample B, which had been prepared by the 100-minutes stirring and therefore appeared to have a higher degree of dispersion, exhibits a lower CV value than that of Sample A. This indicates that Sample B obtained by stirring for a longer time has a higher degree of dispersion.

EXAMPLE 2

| | |
|---|---|
| Organic Material: | |
| Bisphenol A type epoxy resin | 100 parts |
| Inorganic Material: | |
| Spherical silica (average particle size: 5 μm) | 80 parts |

The above materials were stirred in a butterfly mixer for either 5 minutes or 100 minutes to prepare cold-setting compositions Sample C and D, respectively. Each sample was poured into a mold (10×10×5 mm) in a chamber filled with dry air having passed through a calcium chloride-packed tube and then placed in a cooling chamber of a cooling apparatus, where it was cooled to −100° C. to solidify to form Block 3 from Sample C and Block 4 from Sample D.

The whole of each block was diced to a size of 1×1×1 mm by means of a dicer to obtain unit volume pieces 3a, 3b, . . . 3a, 3b, . . . , respectively.

The pieces were individually incinerated at 400° C. for 10 hours. The ash was determined for each piece to a precision of 0.1 μg with an electron balance.

The degree of scatter of the ash content among pieces 3a, 3b, . . . of Block 3 and that among pieces 4a, 4b, . . . of Block 4 were obtained as a CV value. The results obtained are shown in Table 2 below.

TABLE 2

| Sample | Stirring Time (min) | CV Value of Silica Content Among Unit Volume Pieces (%) |
|---|---|---|
| C | 5 | 38.9 |
| D | 100 | 2.2 |

As is apparent from the results in Table 2, Sample D, which had been prepared by the 100-minutes stirring and therefore appeared to have a higher degree of dispersion, exhibits a lower CV value than that of Sample C. This indicates that Sample D obtained by stirring for a longer time has a higher degree of dispersion.

As described above, since the method of the present invention relies on the ash content of a sample as an indication of scatter of an inorganic material in a composite material, the results obtained are quantitative to afford absolute evaluation of the degree of dispersion. There being no possibility that the results may contain any subjective element, improved accuracy of evaluation can be assured. According to the method of the present invention, a dispersion state of a composite material can be grasped substantially throughout the sample.

While the invention has been described in detail and with reference to specific examples thereof, it will be apparent to one skilled in the art that various changes and modifications can be made therein without departing from the spirit and scope thereof.

What is claimed is:

1. A method for evaluating a degree of dispersion of an inorganic material in a composite material comprising an organic material having dispersed therein said inorganic material, said method comprising the steps of:

forming a block sample of said composite material;

dividing said entire block sample into a plurality of equal unit volume pieces;

incinerating each of said equal unit volume pieces under an oxidative atmosphere;

quantitatively determining an ash content of each of said equal unit volume pieces; and calculating a scatter value of the inorganic material content within said plurality of equal unit volume pieces.

2. A method according to claim 1 in which the incinerating is carried out at a time and temperature combination within the range of 400° C. to 600° C. for one hour to twenty hours.

3. A method according to claim 2 wherein calculating the scatter value comprises determining the coefficient of variation.

4. A method according to claim 3, in which the quantitatively determining an ash content comprises determining the weight of the ash.

5. A method according to claim 4 wherein the inorganic material is silica and the organic material is an epoxy resin.

6. A method according to claim 1 wherein calculating the scatter value comprises determining the coefficient of variation.

7. A method according to claim 1, in which the quantitatively determining an ash content comprises determining the weight of the ash.

8. A method according to claim 1 wherein the inorganic material is silica and the organic material is an epoxy resin.

* * * * *